(12) United States Patent
Crandall et al.

(10) Patent No.: US 10,231,741 B2
(45) Date of Patent: Mar. 19, 2019

(54) REAMER HANDLE COUPLING

(71) Applicant: Greatbatch Ltd., Clarence, NY (US)

(72) Inventors: Jonathan P. Crandall, Fort Wayne, IN (US); Jia Li, Fort Wayne, IN (US); Kenton A. Walz, Fort Wayne, IN (US); Paul Alejandro, Fort Wayne, IN (US)

(73) Assignee: Viant AS&O Holdings, LLC, Foxborough, MA (US)

( * ) Notice: Subject to any disclaimer, the term of this patent is extended or adjusted under 35 U.S.C. 154(b) by 315 days.

(21) Appl. No.: 15/200,582

(22) Filed: Jul. 1, 2016

(65) Prior Publication Data

US 2017/0000499 A1      Jan. 5, 2017

Related U.S. Application Data

(60) Provisional application No. 62/187,532, filed on Jul. 1, 2015.

(51) Int. Cl.
| *A61B 17/16* | (2006.01) |
| *B23B 31/10* | (2006.01) |
| *B23B 31/11* | (2006.01) |
| *B23B 31/107* | (2006.01) |
| *B23B 31/117* | (2006.01) |
| *A61B 17/00* | (2006.01) |

(52) U.S. Cl.
CPC ........ *A61B 17/1613* (2013.01); *A61B 17/162* (2013.01); *A61B 17/1659* (2013.01); *A61B 17/1666* (2013.01); *B23B 31/1074* (2013.01); *A61B 2017/00477* (2013.01); *B23B 31/117* (2013.01)

(58) Field of Classification Search
CPC . B23B 31/117; B23B 31/1074; A61B 17/162; A61B 17/1666
See application file for complete search history.

(56) References Cited

U.S. PATENT DOCUMENTS

| 5,658,290 A | 8/1997 | Lechot |
| 5,989,257 A * | 11/1999 | Tidwell ............... A61B 17/162 279/30 |
| 7,115,119 B2 | 10/2006 | Desarzens et al. |

(Continued)

OTHER PUBLICATIONS

European Extended Search, Application No. 16177576.2, dated Sep. 15, 2016.

*Primary Examiner* — Nicholas W Woodall
(74) *Attorney, Agent, or Firm* — Grossman, Tucker, Perreault & Pfleger, PLLC (57) ABSTRACT

A coupling mechanism designed to removably attach a reamer to the distal end of a spindle or shaft is disclosed. The coupling comprises a collar having an annular sidewall that defines a collar throughbore, the collar annular sidewall comprising a plurality of spaced part first slots that at least partially extend through the sidewall and a shank disposed within the collar throughbore. The shank is constructed with a shank annular sidewall in which a plurality of spaced apart second slots at least partially extend therethrough. A bias member that provides a bias force in a distal direction that acts on the collar is incorporated within the mechanism. The collar is capable of sliding in an axial direction such that the first and second slots become aligned to secure the cross bar of a reamer therein.

22 Claims, 10 Drawing Sheets

(56) References Cited

U.S. PATENT DOCUMENTS

| | | |
|---|---|---|
| 7,344,565 B2 * | 3/2008 | Seyer ................ A61F 2/34 606/99 |
| 7,513,899 B2 | 4/2009 | Grim |
| 7,955,323 B2 | 6/2011 | Lechot |
| 8,475,460 B1 | 7/2013 | Roger et al. |
| 8,491,586 B2 | 7/2013 | Lechot et al. |
| 9,050,110 B2 | 6/2015 | Turner et al. |
| 2005/0131395 A1 * | 6/2005 | Lechot ............ A61B 17/1666 606/1 |
| 2007/0191854 A1 * | 8/2007 | Grim ............. A61B 17/1666 606/80 |
| 2012/0023733 A1 * | 2/2012 | Cannell ........... A61B 17/1617 29/525.01 |

* cited by examiner

REAMER HANDLE COUPLING

CROSS REFERENCE TO RELATED APPLICATION

This application claims priority from U.S. Provisional Application Ser. No. 62/187,532, filed Jul. 1, 2015.

TECHNICAL FIELD

This invention relates to the art of instruments used in orthopedic surgical procedures. More specifically, this invention relates to a coupling that is used to attach an acetabular reamer to a spindle.

BACKGROUND OF THE INVENTION

Nearly 200,000 hip replacements are performed each year in the United States and the number is expected to continue to grow as the population ages. The usual reasons for hip replacement are osteoarthritis, rheumatoid arthritis and traumatic arthritis, all of which can cause pain and stiffness that limit mobility and the ability to perform daily living activities. Hip replacement surgery is usually performed when other measures (e.g., physical therapy, medications, and walking aids) are unable to overcome the chronic pain and disability associated with these conditions.

Various techniques are used by orthopedic surgeons to perform hip replacements. These include the following approaches: anterior, antero-lateral, posterior, and postero-lateral. The posterior and posteolateral approaches account for approximately 60% to 70% of hip replacement surgeries.

Traditional hip replacement surgery involves the use of a reamer to remove bone and tissue from the acetabulum. During a typical procedure, a reamer is attached to the distal end of a spindle that provides articulation to the device. A coupling located at the spindle distal end facilitates connection of the reamer thereto. Traditional couplings are generally constructed of a bayonet design in which the coupling must be physically manipulated to attach the reamer to the distal end of a spindle. Typically, these prior art couplings require the operator to physically manipulate the coupling mechanism to attach and detach an orthopedic cutting tool, such as a reamer. Manipulation of prior art coupling mechanisms typically require the use of the hands to attach and detach the cutting tool.

Such manipulation of the attachment coupling mechanism is not ideal because physical contact of the coupling and cutting tool could cause either or both of the coupling and the tool to become contaminated. Thus, minimizing physical contact of the coupling and the cutting tool is ideal. Furthermore, physical manipulation of the coupling mechanism hinders a physician's ability to manipulate other devices simultaneously. A multitude of reamers are typically used during a hip replacement surgical procedure to prepare the acetabulum to receive a prosthetic cup. Use of prior art couplings would require each reamer to be physically attached and removed. Thus, it would be much easier and less cumbersome if the operator did not have to physically manipulate the coupling mechanism to attach a cutting tool.

The present invention, therefore, provides a coupling mechanism that does not require physical manipulation to connect an orthopedic cutting tool, such as a reamer, to a spindle or shaft. The coupling mechanism of the present invention is designed to attach an orthopedic cutting tool to the end of a spindle by physical contact of the cutting tool with that of the mechanism.

The coupling mechanism comprises an arrangement of a plurality of slots, each slot having an angled geometry and orientation that are designed to align and secure a cutting tool therewithin. The arrangement and angled geometry of the various slots within the mechanism encourages the engagement of a cross bar driver interface within the coupling. A bias member incorporated within the mechanism provides a bias force that causes the plurality of slots to align, thereby securing the driver interface therewithin. Thus, a cutting tool can be attached to the end of a spindle by physical contact of the driver interface of the tool with the coupling mechanism, thus eliminating the need to manipulate the mechanism by hand.

SUMMARY OF THE INVENTION

The present invention provides a coupling mechanism that is designed to attach and detach an orthopedic cutting tool, such as a reamer to the distal end of a spindle or shaft. The mechanism of the present invention comprises a plurality of slots that work together to secure an orthopedic cutting tool therewithin. In a preferred embodiment, the coupling comprises a collar that circumferentially extends about a stationary shank. The collar comprises an annular sidewall within which a plurality of spaced apart first slots reside. The shank comprises an annular sidewall in which a plurality of spaced apart second slots reside. The collar is capable of moving in an axial direction along a longitudinal axis of the shank.

A bias member is positioned within the coupling mechanism that provides a bias force that acts against the collar. The bias force causes the collar to slide in a distal direction such that the first and second slots become aligned so that a driver interface, such as a cross bar of an orthopedic cutting tool, becomes captured therewithin. The first and second slots of the collar and shank are constructed in a specific angular relationship so that physical contact between the coupling and the driver interface causes the collar to slide in a proximal direction so that the cross bar becomes captured within the slots. The cross bar of the attachment member of the cutting tool can be removed by moving an outer collar in a proximal direction such that the cross bar of the attachment member and the orthopedic cutting tool disengages from the coupling mechanism.

DETAILED DESCRIPTION OF THE PREFERRED EMBODIMENT

Figure 1:
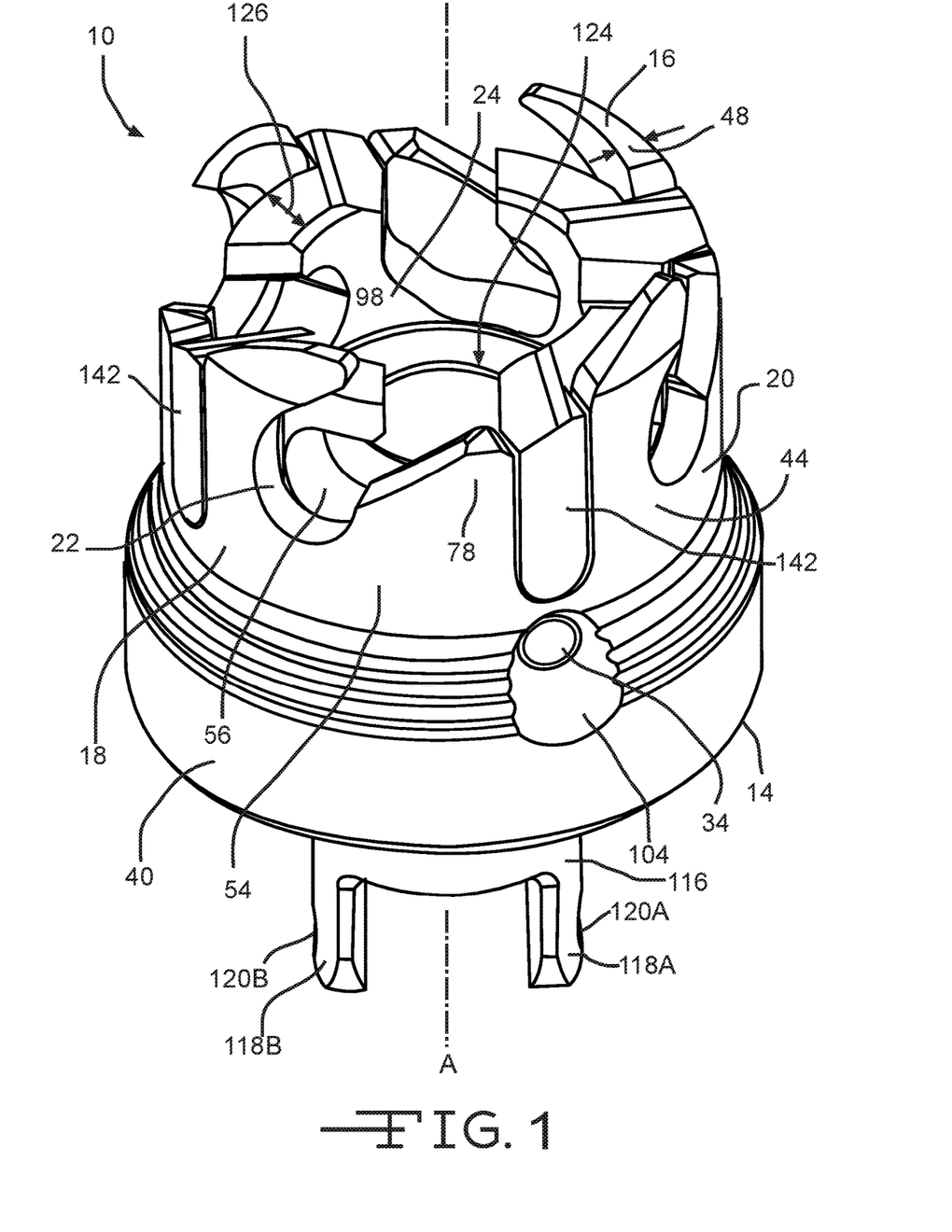
FIG. 1 illustrates a perspective view of an embodiment of the coupling mechanism of the present invention in a first position.
Figure 2:
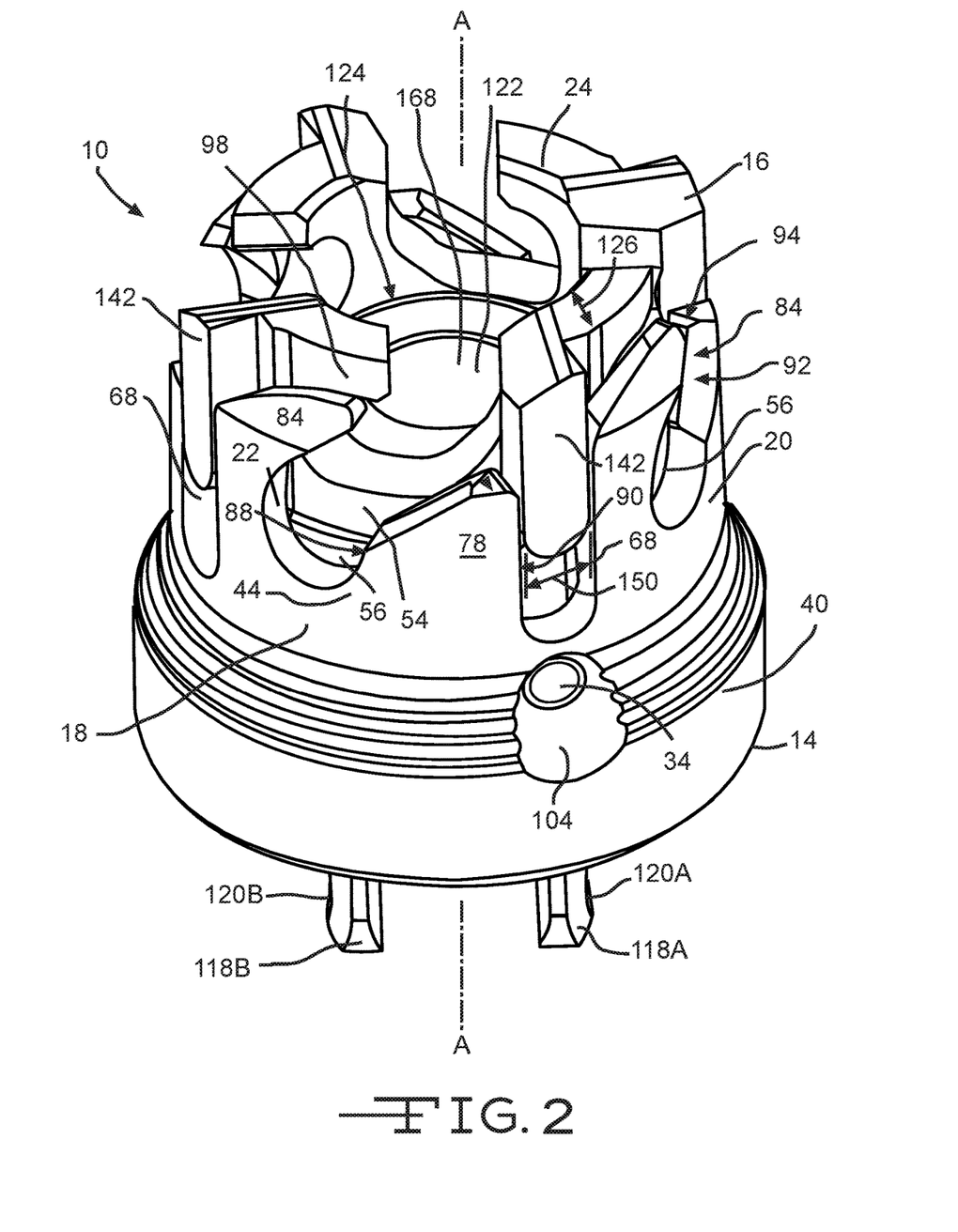
FIG. 2 is a perspective view of the embodiment of the coupling mechanism shown in FIG. 1 in a second position.
Figure 3:
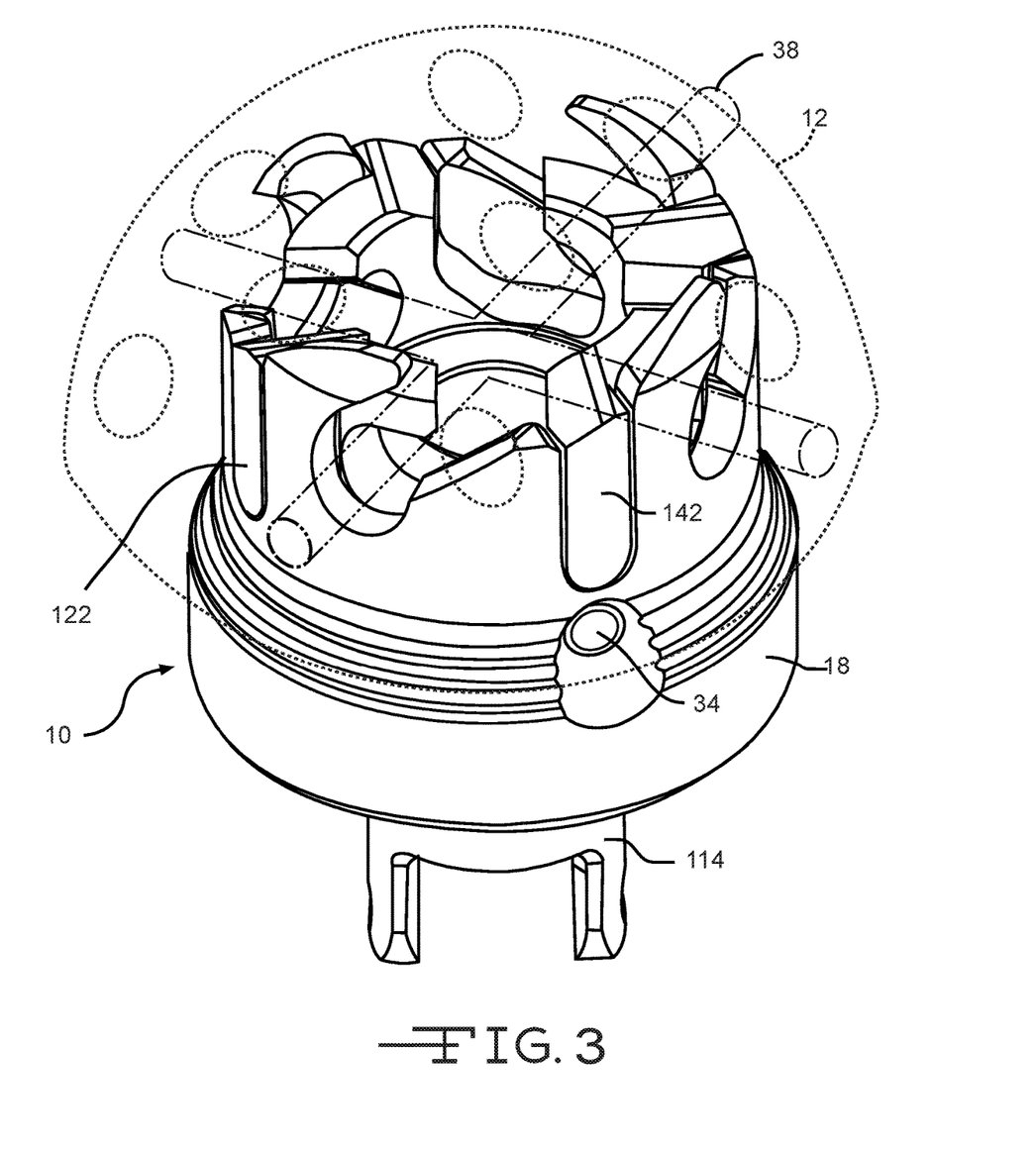
FIG. 3 illustrates a perspective view of an embodiment of the coupling mechanism shown in FIGS. 1 and 2 in which an orthopedic cutting tool is secured therewithin.

Now turning to the figures, FIGS. 1-3 illustrate a preferred embodiment of a coupling mechanism 10 of the present invention. The coupling mechanism 10 is used to removably secure an orthopedic cutting tool 12 such as a reamer (FIG. 3) to a spindle 202 (FIG. 8) for manipulation during a surgical procedure. The coupling mechanism 10 extends lengthwise along longitudinal axis A-A from a proximal end 14 to a distal end 16. As illustrated in FIGS. 1-3, the mechanism 10 comprises a collar 18 having a collar annular sidewall 20 with a plurality of spaced apart first slots 22 that extend part-way through the collar annular sidewall 20, a shank 24 having a shank annular sidewall 26 with a plurality of spaced apart second slots 28 (FIG. 4) that extend part-way through the shank annular sidewall 26, and a collar connection sub-assembly 30 (FIG. 5) comprising a bias 32 and a pin 34.

The shank 24 is preferably disposed within a throughbore 36 that is defined by the collar annular sidewall 20. The shank 24 is positioned within the collar throughbore 36 such that collar 18 is slidable in an axial direction along longitudinal axis A-A with respect to the shank 24. The collar 18 is preferably oriented about the shank 24 such that the openings of the first and second slots 22, 28 of the collar 18 and shank 24, respectively, align as the collar 18 slides in an axial direction along longitudinal axis A-A about the shank 24. The collar connection subassembly 30 connects the collar 18 to the shank 24 and, in addition, provides a bias force against the collar 18 in a distal direction. In a preferred embodiment, a driver interface 38 of an orthopedic cutting tool 12 (FIG. 3), such as a cross bar of an orthopedic reamer, is removably engaged and secured within the openings of the first and second slots 22, 28 of the collar 18 and shank 24, respectively.

Figure 6:
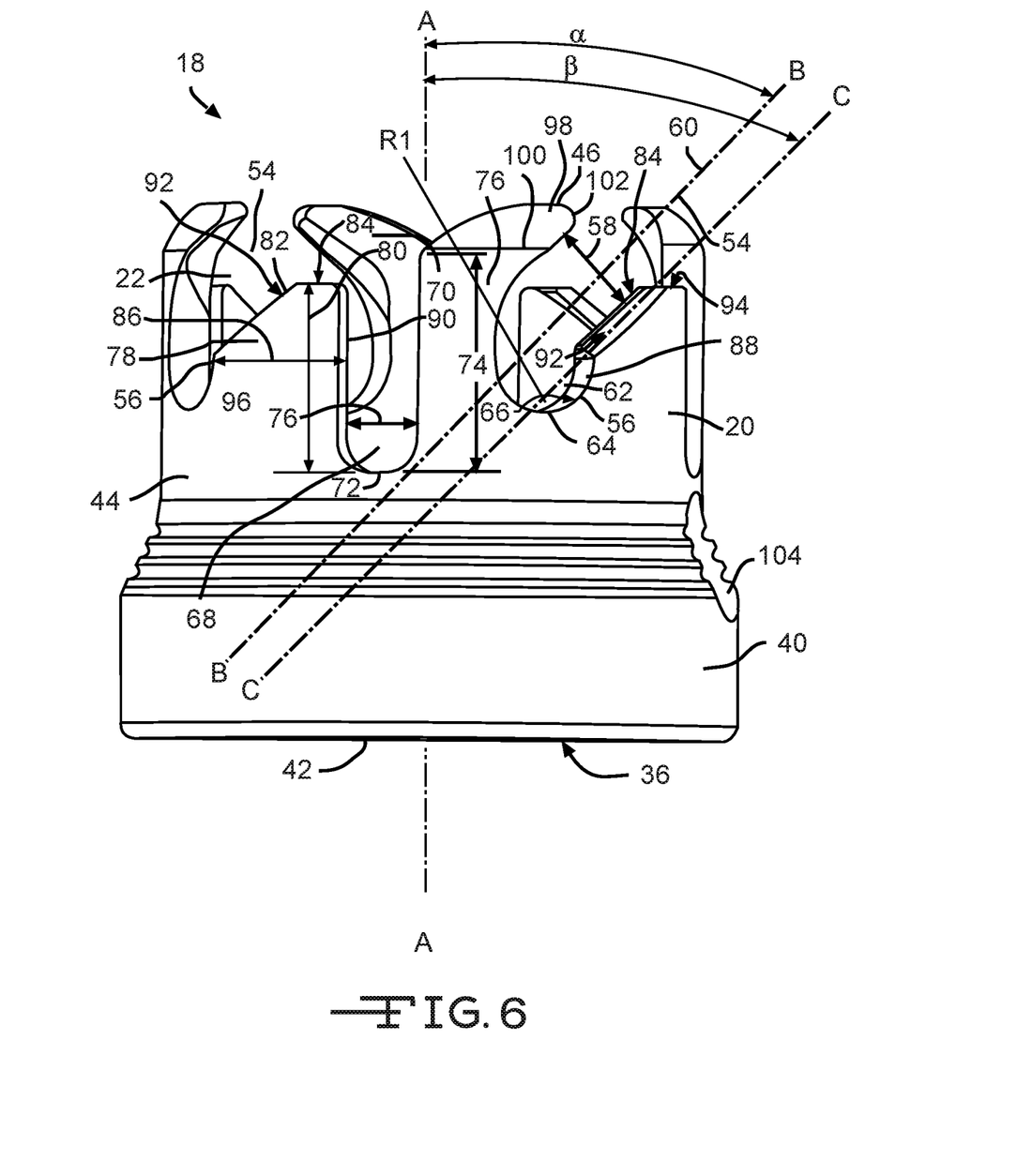
FIG. 6 is a perspective view of an embodiment of a collar component of the coupling mechanism shown in FIG. 1.

FIG. 6 illustrates an embodiment of the collar 18 of the coupling mechanism 10 of the present invention. As illustrated, the collar 18 extends lengthwise along longitudinal axis A-A from a collar proximal portion 40 having a collar proximal end 42 to a collar distal portion 44 having a collar distal end 46. In a preferred embodiment, each of the plurality of spaced apart first slots 22 extends part way through the annular sidewall 20 of the collar distal portion 44. As shown, each of the plurality of first slots 22 extends through an annular sidewall thickness 48 that spans between an annular sidewall interior surface 50 and an annular sidewall exterior surface 52 at the collar sidewall distal end 46. In addition, each of the plurality of first slots 22 extends part-way from the collar distal end 46 towards the collar proximal sidewall end 42.

In a preferred embodiment, each of the plurality of first slots 22 comprises a first slot opening portion 54 that transitions to a first slot capture portion 56. As illustrated in FIG. 6, the first slot opening portion 54 extends through the thickness 48 of the collar annular sidewall at the distal end 46 towards the collar proximal end 42 where it meets the first slot capture portion 56. The first slot opening portion 54 forms an opening within the thickness of the collar annular sidewall 20 that is dimensioned to receive at least a portion of a driver interface 38, such as a cross bar of a reamer. In an embodiment, the opening formed by the first slot opening portion 54 has a width 58 that ranges from about 0.1 cm to about 1 cm. In addition, the first slot opening portion 54 is oriented at an angular relationship with respect to longitudinal axis A-A. In an embodiment, the first slot opening portion 54 is oriented at angle α which extends between imaginary plane B-B that bisects the width 58 of the first slot opening portion 54 and longitudinal axis A-A. In a preferred embodiment, angle α ranges from about 30° to about 60°, more preferably, angle α is about 45°.

As illustrated in FIGS. 1-4 and 6, the capture portion 56 of the first slot 22 extends in a proximal direction partway within the collar annular sidewall 20. In an embodiment, the first slot capture portion 56 extends about parallel to longitudinal axis A-A from a proximal end 60 of the first slot opening portion 54. As illustrated in FIG. 6, the capture portion 56 of the first slot 22 forms a well 62 within which a cross bar from the driver interface 38 of an orthopedic cutting tool 12 fits therewithin. In a preferred embodiment, the first slot capture portion 56 extends to a first slot proximal end 64 having a first slot proximal end surface 66 that is curved. In a preferred embodiment, as illustrated in FIG. 6, the first slot capture surface 66 has a radius of curvature $R_1$ that ranges from about 0.1 cm to about 2 cm. The curved first slot capture surface 66 created by the first slot capture portion 56 is designed to receive a cross bar having a curved structure from the driver interface 38 of an orthopedic cutting tool 12.

In an embodiment, the collar 18 comprises a plurality of spaced apart alignment slots 68. Each slot 68 extends through the thickness of the collar annular sidewall and is bisected by a plane aligned longitudinally along longitudinal axis A-A. The slot 68 extends part way towards the collar annular sidewall proximal end 42. As illustrated in FIGS. 1-3, and 6, each of the plurality of alignment slots 68 extends longitudinally between adjacent first slots 22 of the collar annular sidewall 20. In a preferred embodiment, each of the plurality of alignment slots 68 comprises an alignment slot open distal end 70, spaced from the collar distal end 46, the opening extending part way along the length of the collar 18 to an alignment slot proximal end 72 spaced from the collar proximal end 42. In a preferred embodiment, the alignment slot 68 has a length 74 extending along longitudinal axis A-A that ranges from about 0.5 cm to about 5 cm and a width 76 oriented perpendicular to the alignment slot length 74 that ranges from about 0.5 cm to about 5 cm.

As illustrated in FIGS. 1-4, and 6, the collar 18 comprises a plurality of first posts 78, each first post 78 is formed between a first slot 22 and an alignment slot 68. In a preferred embodiment, the first post 78 has a length 80 that extends along longitudinal axis A-A from the proximal end 72 of the alignment slot 68 to a first post distal end 82 having a plateau end surface 84. In a preferred embodiment, the first post 78 has a width 86 that extends between respective left and right first post surfaces 88, 90. The first post left sidewall surface 88 is formed by the first slot capture portion 56 and the first post right sidewall surface 90 is formed by the alignment slot 68.

The first post distal end surface 84 is preferably oriented at an angular relationship with respect to longitudinal axis A-A. In a preferred embodiment, the first post comprises an angled surface 92 that extends distally towards and meeting the plateau distal end surface 84 of the first post 78. The angled surface 92 of the first post 78 is formed by the opening portion 54 of the first slot 22. In a preferred embodiment, the plateau surface 84 extends about perpendicular to longitudinal axis A-A and meets the right sidewall surface 90 of the first post 78. The angled surface 92 of the first post 78 extends from the sidewall surface 88 and in an upwardly direction to the plateau 84. As illustrated in FIG. 6, the angled surface 92 of the first post 78 slopes downward towards the capture portion 56 of the first slot 22. In a preferred embodiment, the angled distal end surface 92 is oriented at angle β which spans between an imaginary plane C-C, intersecting longitudinal axis A-A. Angle β may range from about 30° to about 60°, more preferably 45°. The downward angle of the angled surface 92 encourages a cross bar from the driver interface 38 of a cutting tool 12 to slide in a downward proximal direction towards the first slot capture portion 56 where it is captured therewithin.

In addition, as illustrated in FIGS. 1-4 and 6, the collar 18 comprises a plurality of second posts 96, each second post 96 is formed between the right sidewall of the alignment slot 68 and the first slot 22. As illustrated the second post 96 extends lengthwise from the proximal end 72 of the collar alignment slot 68 towards the distal end 46 of the collar 18. A prong 98 outwardly extends from a distal end 100 of the second post 96 to a prong point 102. The angled orientation of the prongs 98 encourages the positioning of the cross bar of the driver interface 38 of an orthopedic cutting tool 12 within the first and second slots 22, 28 of the coupling 10.

Figure 4:
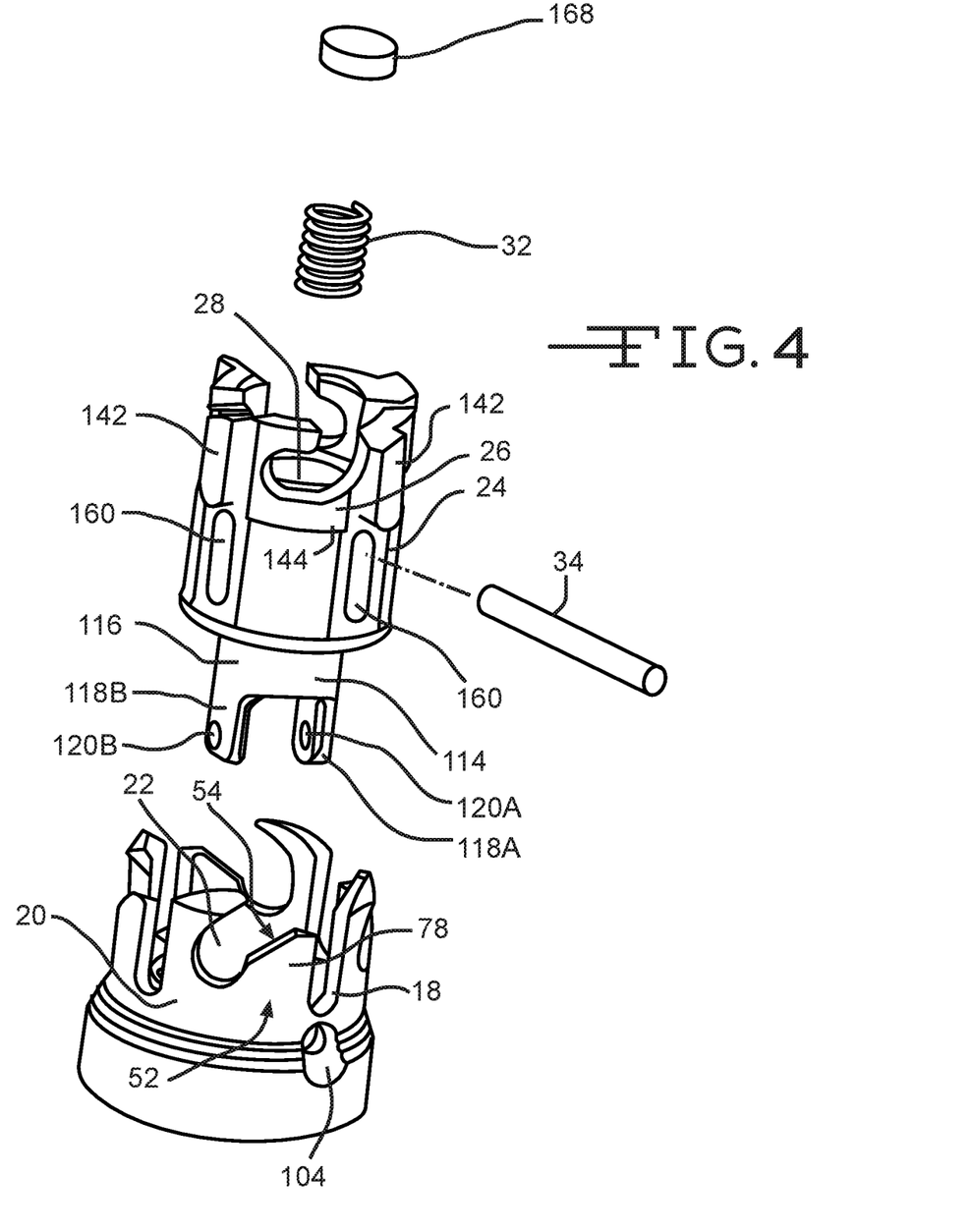
FIG. 4 shows an exploded view of the coupling mechanism shown in FIG. 1.
Figure 5:
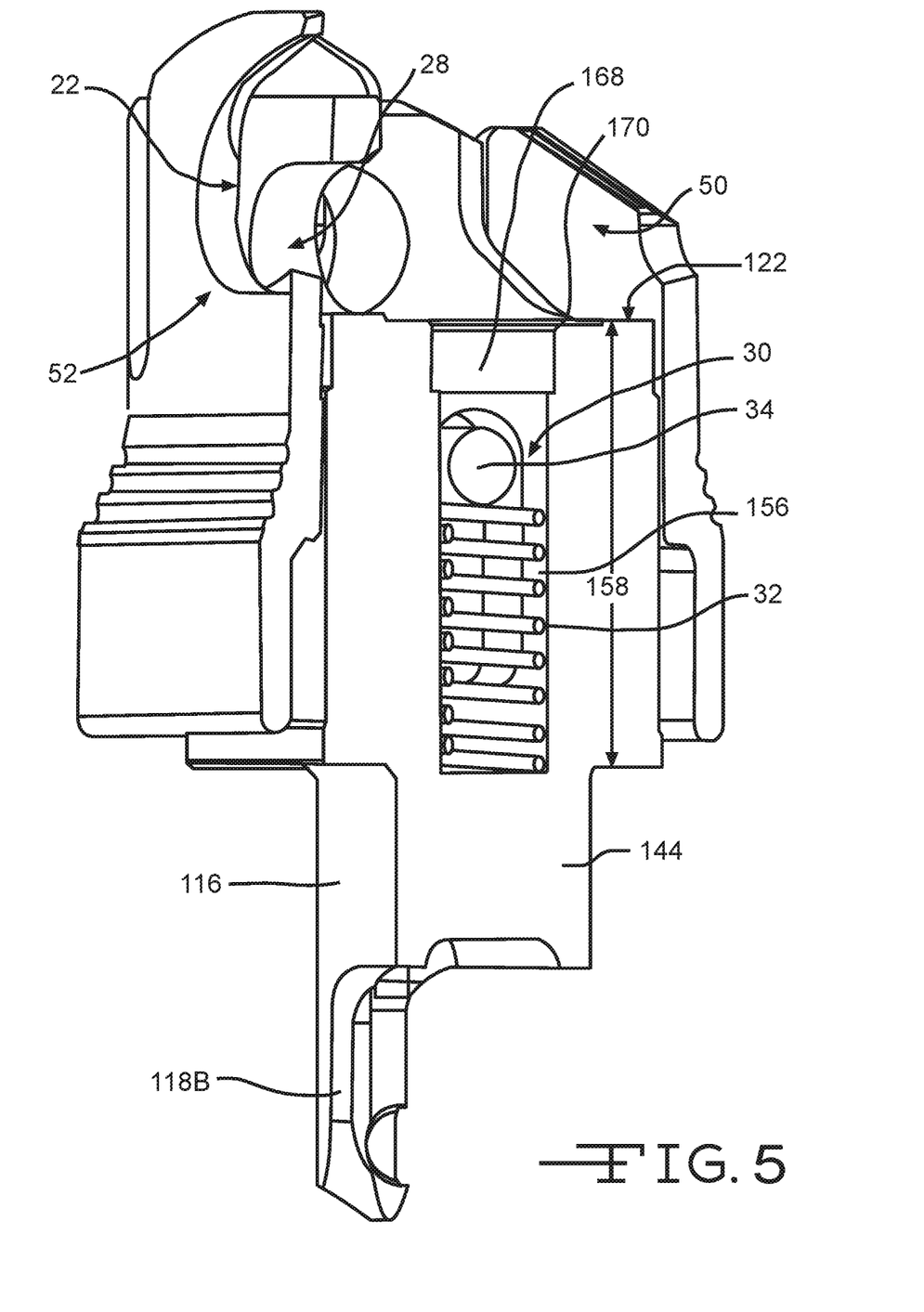
FIG. 5 is a cross sectional view of the coupling mechanism shown in the embodiment of FIG. 1.

At least one pair of spaced apart openings 104 extend through the distal portion of the coupling annular sidewall 20 in opposition to each other. As shown in FIGS. 4 and 5, each opening 104 preferably extends through the thickness of the distal portion 44 of the collar annular sidewall 20 perpendicular to longitudinal axis A-A. The openings 104 preferably reside within the distal portion of the annular collar sidewall spaced from the proximal end 42 of the collar annular sidewall 20. In a preferred embodiment, each of the openings 104 are dimensioned to receive an end of the pin 34 of the collar connection subassembly 30, thereby providing a mechanical connection between the collar 18 and the shank 24.

FIGS. 1-4 and 7 illustrate an embodiment of the shank 24 that is incorporated within the coupling 10 of the present invention. As shown, the shank 24 extends lengthwise along longitudinal axis A-A from a shank proximal portion 106 having a shank proximal end 108 to a shank distal portion 110 having a shank distal end 112. A U-joint 114 comprising a cylindrical side wall 116 supporting a pair of yoke plates 118A and 118B having respective openings 120A, 120B extends from the proximal end 108 of the shank 24. The U-joint 114 provides a means of connecting the shank 24 and the coupling assembly 10 to a spindle 202 (FIG. 8).

The shank annular sidewall 26 extends in a distal direction towards the shank distal end 112 from a platform surface 122 (FIG. 2) that resides at the distal end of the proximal portion 106 of the shank 24. The shank sidewall 26 is positioned annularly about the perimeter of the shank 24 such that the annular sidewall 26 defines an opening 124 within which a driver interface 38, such as a cross bar of an orthopedic cutting tool 12 is received.

In a preferred embodiment, as illustrated in FIGS. 1-4 and 7, the plurality of second slots 28 are each formed within a thickness 126 of the shank annular sidewall 26. Each second slot 28 extends through the distal end 112 of the shank annular sidewall 26 and along a length 128 to a position distal of the platform surface 122. In a preferred embodiment, each second slot 28 comprises a second sidewall cutout portion 130 that transitions to a second sidewall traverse portion 132. The cutout portion 130 extends through the distal end 112 of the shank annular sidewall 26 where it meets the traverse portion 132 residing within the thickness of the annular shank sidewall 26. In a preferred embodiment, the cut out portion 130 is oriented about parallel to longitudinal axis A-A. The traverse portion 132 is oriented about perpendicular to longitudinal axis A-A. In an embodiment, an overhang portion 134 resides distal of the traverse portion 132 of the second slot 28. Thus, the second slot traverse portion 132 resides between the platform surface 122 and the overhang portion 134 such that the cross bar of a driver interface 38 of an orthopedic cutting tool 12 can be captured within the space provided therewithin.

Figure 7:
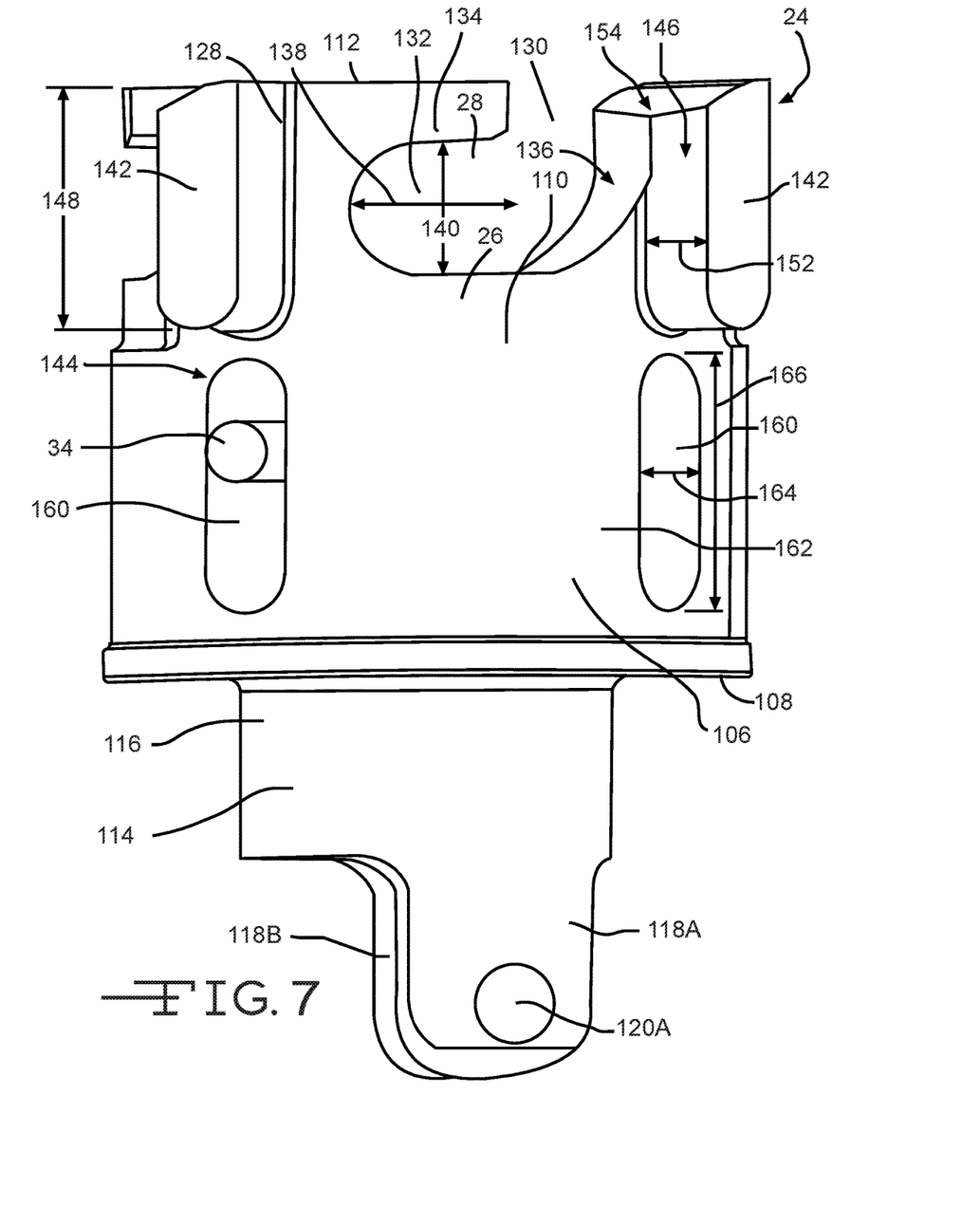
FIG. 7 illustrates a perspective view of an embodiment of a shank component of the coupling mechanism illustrated in FIG. 1.
Figure 8:
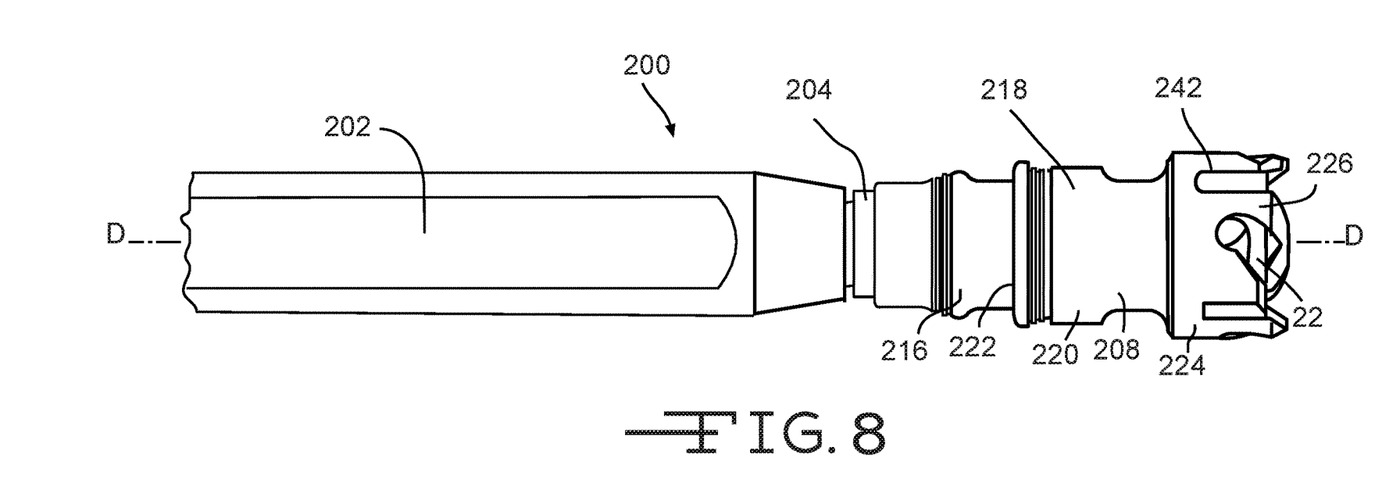
FIG. 8 is a side view of an alternate embodiment of the coupling mechanism of the present invention.

In a preferred embodiment, as illustrated in FIG. 7, the slot surface 136 formed by the cutout portion 130 is curved. In a preferred embodiment, surface 136 of the cutout portion 130 has a downward slope to a base surface of the traverse portion 132 of the second slot 28. The curved surface 136 encourages a driver interface 38, such as the cross bar of a reamer, to slide within the traverse portion 132 to reside therewithin. In a preferred embodiment, the transverse portion has a length 138 that extends from about 0.5 cm to about 5 cm about perpendicular to longitudinal axis A-A and a width 140 that ranges from about 0.5 cm to about 3 cm. In an embodiment, the length 138 and width 140 of the transverse portion 130 are dimensioned such that a cross-bar is able to be received therein.

As shown in FIGS. 1-4 and 7, the shank 24 comprises a plurality of protrusions 142 each of which extends outwardly from an exterior surface 144 of the annular sidewall 26. The shank protrusions 142 serve as an alignment guide with respect to the collar 18. Alignment occurs when a protrusion 142 is received within a corresponding alignment slot 68 extending longitudinally through the collar annular sidewall 20. The mating of the protrusion 142 and corresponding alignment slot 68 helps ensure that the respective first and second slots 22, 28 are properly aligned, particularly as the collar 18 moves in an axial direction with respect to the shank 24.

In a preferred embodiment, as shown in FIGS. 1-4 and 7, each of the plurality of protrusions 142 is positioned lengthwise between adjacent second slots 28. In a preferred embodiment, each of the plurality of protrusions 142 is positioned spaced about the exterior of the shank 24 such that an elongated sidewall surface 146 that extends along the length of the protrusion meets the curved surface 136 of the second slot 28 formed by the cutout portion 130. In an embodiment, the alignment protrusion 142 comprises a length 148 that extends about parallel to the longitudinal axis A-A, and a width 150 that extends about perpendicular to the length 148. In a preferred embodiment, the length 148 may range from about 0.5 cm to about 3 cm and the width 150 may range from about 0.1 cm to about 2 cm. In a preferred embodiment, the alignment protrusion 142 comprises a protrusion thickness 152 that outwardly extends from the exterior surface 144 of the shank annular sidewall 26. In a preferred embodiment, thickness 152 may range from about 0.1 cm to about 3 cm. The distal end of the protrusion 142 may have a curved surface 154 that slopes in downward or proximal direction towards the cutout portion 130 of the second slot 28. This downward slope of the protrusion 142 helps encourage the cross bar of a driver interface 38 to be positioned within the second slot 28.

As illustrated in FIGS. 4 and 5, the bias 32 and the pin 34 of the collar connection sub-assembly 30 are preferably positioned within a cavity 156 formed within the proximal portion 106 of the shank 24. The bias 32 may comprise a spring or coil. In a preferred embodiment, the cavity 156 extends longitudinally within the shank 24 through the platform surface 122 in a proximal direction to a position distal of the shank proximal end 108. In a preferred embodiment, the cavity 156 has a depth 158 that ranges from about 1 cm to about 10 cm and a diameter that ranges from about 1 cm to about 5 cm.

In a preferred embodiment, as illustrated in FIG. 4, a plurality of spaced apart third slots 160 are formed circumferentially spaced apart around the proximal portion 106 of the shank 24. In a preferred embodiment, each third slot 160 is oriented lengthwise about parallel to longitudinal axis A-A and extending through a proximal portion sidewall 162 and widthwise through the thickness of the shank proximal portion 106 to thereby meet the cavity 156 therewithin. In a preferred embodiment, the plurality of third slots 160 are arranged about the cavity 156 and through the shank proximal portion 106 such that two of them are positioned in opposition to each other. The shank proximal portion 106 is constructed such that the pin 34 of the collar connection subassembly 30 is oriented lengthwise perpendicular to longitudinal axis A-A such that the pin 34 extends through the width of the cavity 156 with the spaced apart first and second ends of the pin 34 extending through opposing third slots 160. The respective first and second ends of the pin 34 are positioned within the opposing third slots 160 such that the pin 34 can travel in an axial direction along the length of the opposed third slots 160. In a preferred embodiment, the pin 34 is positioned distal of the bias member 32 within the cavity 156 of the proximal portion 106 of the shank 24. The bias member 32 generates a bias force in a distal direction against the pin 34. A cap 168 is preferably positioned within a cavity opening 170 that extends through the platform surface 122. The cap 168 serves to encase the pin 34 and bias 32 of the subassembly 30 within the proximal portion 106 of the shank 24.

FIGS. 1-3 illustrate an embodiment of the assembled coupling mechanism 10 of the present invention. As shown, the shank proximal portion 106 (FIG. 7) is positioned within the throughbore 36 of the collar 18. The pin 34 of the subassembly 30 extends through the proximal portion 106 of the shank 24 with the opposing first and second pin ends each received in respective openings 104 within the proximal portion 40 of the collar 18, thereby securing the shank 24 to the collar 18. In addition, the subassembly 30 provides a bias force that acts on the pin 32 and the collar 18 in a distal direction thereby causing the collar 18 to move axially in a distal direction with respect to the shank 24.

The collar 18 and shank 24 of the coupling mechanism 10 are assembled together such that each of the plurality of protrusions 142 that outwardly extend from the exterior surface of the shank 24 is received within a corresponding alignment slot 68 of the collar 18. The shank protrusion 142 rides within the collar alignment slot 68 as the collar 18 moves in an axial direction along longitudinal axis A-A with respect to the shank 24. When the distal end of the protrusion 142 comes into contact with the bottom proximal surface of the alignment slot 68, the collar 18 has reached its most distal position with respect to the shank 24, and the respective openings of the traverse portion 132 of the second slot 28 and the capture portions 56 of the first slot 22 become aligned.

In addition, when the collar 18 is in the distal-most position, the first post 78 of the collar 20 is aligned with the cutout portion 130 of the shank 24, thus securing at least a portion of a driver interface 38, such as the cross bar of a reamer, therewithin, as illustrated in FIG. 3. The bias force created by the bias member 32 acts on the collar 18 in a distal direction to help keep the collar 18 in the distal-most position. Conversely, the driver interface 38 can be removed from the coupling mechanism 10 by moving the collar 18 in a proximal direction in opposition to the bias force. Proximal movement of the collar 18 with respect to the shank 24 moves the first post 78 away from the cutout portion of the second slot 28 thereby enabling the driver interface 38 to be removed from the coupling 10.

FIGS. 1 and 3 illustrates an embodiment in which the collar 18 is oriented in a first position or distal-most position. As illustrated, when the collar 18 and shank 24 of the coupling mechanism 10 are positioned in the first position, the capture portion 56 of the first slot 22 and the traverse portion 132 of the second slot 28 are aligned. The first post 78 of the collar 18 is positioned such that it blocks the opening created by the cutout portion 130 of the second slot 28. This first position, as illustrated in FIG. 3, in which the capture portion 56 of the first slot 22 of the collar 18 is aligned with the traverse portion 132 of the second slot 28 of the shank 24, is the position in which the cross bar of a driver interface 38 of an orthopedic cutting tool 12 is captured and secured therewithin. As shown, the first post 78 of the collar 18 traps the cross bar within the capture portion 56 of the first slot 22 and traverse portion 132 of the second slot 28, thus preventing it from moving out of the mechanism 10. The cross bar and orthopedic cutting tool can be released from the coupling 10 by moving the collar 18 in a proximal direction so that the first post 78 is moved in a proximal direction away from the cutout portion 132 of the second slot 28, thereby enabling the cross bar to move from the traverse portion 132 to the cutout portion 130 of the second slot 28 and disengage from the coupling 10.

In addition, the coupling mechanism 10 of the present invention is designed such that a cross bar of a driver interface 38 of an orthopedic cutting tool 12 can become engaged without physical manipulation by an operator. In a preferred embodiment, physical contact of at least a portion of a driver interface 38 of an orthopedic cutting tool 12, such as the cross bar driver interface, with the downwardly angled distal end surface 84 of the first post 78 causes the collar 18 to slide in a proximal direction in opposition to the bias force, thereby exposing the cutout portion 130 of the second slot 28 blocked by the first post 78 when the collar 18 is positioned in its initial, first position (FIGS. 1 and 3). As the collar 18 slides in an axial direction towards the coupling proximal end 14, the second slot cutout portion 130 is revealed which allows the cross bar to enter the groove created by the second slot 28. This is the coupling second position as illustrated in FIG. 2. Once the cross bar is received within the traverse portion 132 of the second slot 28, the bias force created by the bias member 32 within the shank 24 acts on the collar 18 to slide it axially in a distal direction along longitudinal axis A-A to its first position or distal-most as shown in FIGS. 1 and 3. As the collar moves along longitudinal axis A-A in a distal direction, the post 78 returns to its initial starting positioned to block the second slot cutout opening 130, thereby securing the cross bar therewithin.

FIGS. 8-11 illustrates an alternate embodiment of a coupling mechanism 200 of the present invention that is used to removably secure an orthopedic cutting tool 12 such as a reamer (FIG. 3) to a spindle 202 (FIGS. 8 and 9) for manipulation during a surgical procedure. The coupling mechanism 200 extends lengthwise along longitudinal axis D-D from a proximal end 204 to a distal end 206. The mechanism 200 comprises a collar 208, a shank 210 and a collar connection sub-assembly 212 comprising a bias member 214 and a locking ring 216. As illustrated, the collar 206 comprises an collar annular sidewall 218 that extends from a sidewall proximal portion 220 with a sidewall proximal end 222 to a sidewall distal portion 224 with a sidewall distal end 226. A plurality of spaced apart first slots 22 extend part-way through the distal portion 224 of the collar annular sidewall 218. The shank 210 comprises an elongated proximal portion 228 having a shank proximal end 230 that extends along longitudinal axis D-D towards a shank distal portion 232 having a shank distal end 234. The shank distal portion comprises an annular shank sidewall 236 having a plurality of spaced apart second slots 28 extending part-way through the annular shank sidewall 236. As shown, a spindle rod 238 may be connected to the proximal end 230 of the shank 210. Alternatively, the spindle rod 238 and the shank 210 may be formed of one piece.

Similar to the coupling mechanism 10 of the previous embodiment, the shank 210 is disposed within a throughbore 240 of the collar 208 with the collar 208 designed to move in an axial direction along longitudinal axis D-D with respect to the shank 210. In addition, the distal portions of the collar 208 and shank 210 of the mechanism 200 have the same construction as the respective collar 18 and shank 24 of the coupling mechanism 10. Specifically, the first and second slots 22, 28 of the collar 208 and shank 210, respectively, of the coupling mechanism 200 are of the same construction having the same dimensions, angular relationship and position as the first and second slots 22 and 28 of the collar 18 and shank 24 of the coupling mechanism 10 of the previous embodiment. Furthermore, the coupling mechanism 200 comprises a collar alignment slot 68 and shank protrusion 112 that are of the same construction having the same dimensions, angular relationship and position as that of the coupling mechanism 10 of the previous embodiment. Like the coupling mechanism 10, the shank protrusion 112 rides within the collar alignment slot 68. A bias force generated by the bias member 214 acts on the collar 208 in a distal direction to thereby bring the first and second slots 22, 28 closer together so that at least a portion of a driver interface 38 such as the cross bar of a reamer is captured therebetween.

Figure 9:
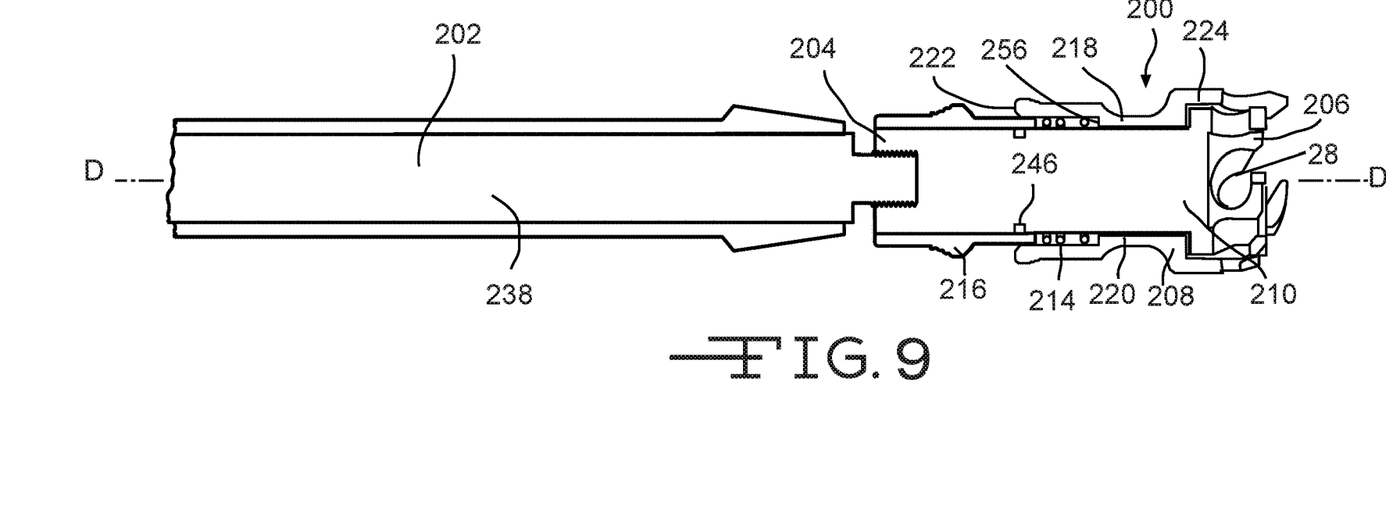
FIG. 9 illustrates a cross-sectional view taken lengthwise of the coupling mechanism shown in FIG. 8.
Figure 10:
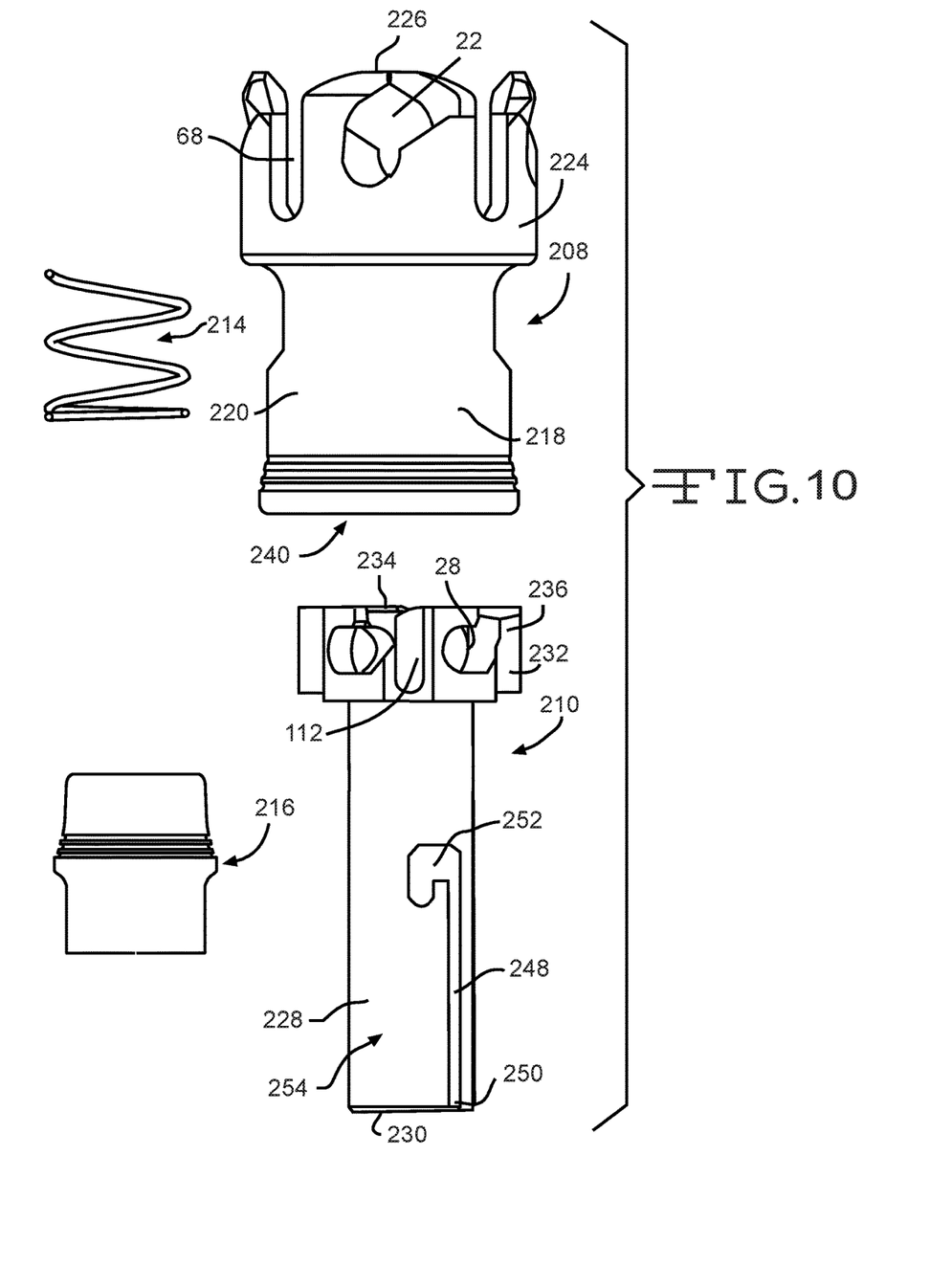
FIG. 10 is an exploded view of the coupling mechanism shown in FIG. 8.

As illustrated in FIG. 9, the locking ring 216 of the collar connection sub-assembly 212 of the coupling mechanism 200 comprises an annular locking ring sidewall 242 having spaced apart interior and exterior ring sidewall surfaces 243, 245 define a throughbore 244 that extends along longitudinal axis D-D. At least one locking protrusion 246 extends outwardly from the interior sidewall surface 243 towards longitudinal axis D-D.

As illustrated in FIGS. 8-11, the proximal portion 228 of the shank 210 is received within the locking ring throughbore 244. The locking ring protrusion 246 is positioned within a locking groove 248 that extends from a locking groove proximal end 250 at the proximal end 230 of the shank 210 to a locking groove distal end 252 spaced from the distal end of the shank proximal portion 228. The locking groove 248 at least partially extends within an exterior surface 254 of the proximal portion 228 of the shank 210. The locking groove 248 preferably extends longitudinally from a locking groove proximal end towards the shank distal portion 232 were the locking groove 248 forms a hook end having an I-shape in which the locking groove 248 extends in a perpendicular direction to longitudinal axis D-D and then in a proximal direction part way to the shank proximal end 230.

Figure 11:
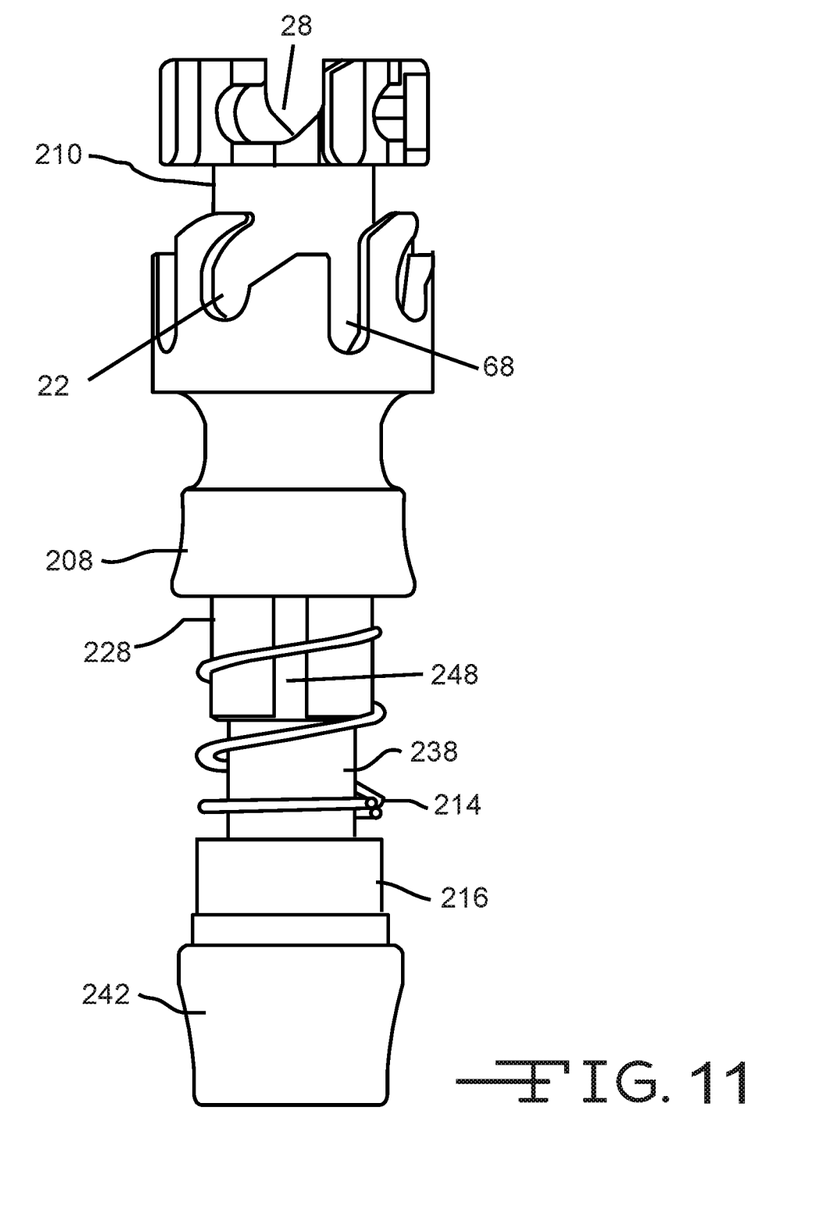
FIG. 11 is a perspective view that illustrates the assembly of the coupling mechanism of FIG. 8.

As illustrated in FIGS. 9 and 11, the proximal portion 228 of the shank 210 is positioned through the locking ring through bore 244. The bias member 214 is position circumferentially around the proximal portion 228 of the shank 210 distal of the locking ring protrusion 246. In a preferred embodiment, the locking ring protrusion 246 is aligned within the locking groove 248 of the shank proximal portion and moved in a proximal direction such that it becomes "locked" within the groove of the I-shaped hook end. The bias member 214 thus resides between the locking ring protrusion 246 and a ledge 256 that outwardly extends from an interior collar surface. The bias member therefore becomes compressed between the collar 208 and the locking ring 216 thereby providing a bias force in a distal direction that acts on the collar.

Thus, similar to the coupling mechanism 10 of the previous embodiment, the bias force provided by the bias member 214 acts on the collar 208 in a distal direction such that at least a portion of the driver interface 38 is captured within the first and second slots 22, 28 of the collar 208 and shank 210, respectively. Likewise, similar to the coupling mechanism 10 of the previous embodiment, the collar 208 is moved in a proximal direction to release the driver interface 38.

While the preferred embodiments of the coupling tool and methods have been described in reference to the environment in which they were developed, they are merely illustrative of the principles of the inventions. Other embodiments and configurations may be devised without departing from the spirit of the inventions and the scope of the appended claims.

What is claimed is:

1. A mechanism for connecting an instrument to a driver, the mechanism comprising:
   a) a collar comprising a collar annular sidewall defining a collar throughbore that extends along a longitudinal axis A-A from a collar proximal portion having a collar proximal end and a collar annular sidewall proximal end to a collar distal portion having a collar distal end and a collar annular sidewall distal end, the collar annular sidewall having a collar annular sidewall thickness spaced between an interior collar sidewall surface and an exterior collar sidewall surface, wherein at least two spaced apart first slots extend through the collar annular sidewall thickness from the collar annular sidewall distal end part way to the collar annular sidewall proximal end and wherein an alignment slot extends longitudinally through the collar annular sidewall distal end partway to the collar proximal end;
   b) a shank having a shank proximal portion with a shank proximal end that extends along the longitudinal axis A-A to a shank distal portion having a shank distal end, a cavity residing within the shank proximal portion and a shank annular sidewall that extends from the shank proximal portion to the shank distal end, the shank annular sidewall having a shank annular sidewall thickness that extends perpendicular to the longitudinal axis, wherein:
      a. at least two spaced apart second slots extend through the shank annular sidewall thickness from the shank annular sidewall distal end part way to the shank annular sidewall proximal end;
      b. the shank is disposed within the collar throughbore so that the collar is slidable in an axial direction along the longitudinal axis A-A with respect to the shank, the respective proximal and distal portions of the shank and collar oriented in parallel to the longitudinal axis A-A; and
      c. a protrusion outwardly extends from an exterior surface of the shank, the protrusion extending longitudinally from a protrusion distal end at the shank distal end to a protrusion end spaced from the shank proximal end, wherein the protrusion is received within the alignment slot;
c) a pin having opposed first and second pin ends disposed within the shank cavity, wherein the first and second pin ends extend through opposing third slots that extend through a thickness of the shank proximal portion perpendicular to the longitudinal axis, and wherein the respective first and second pin ends are connected to the collar annular sidewall; and
d) a bias member disposed within the shank cavity proximal of the pin, wherein the bias member provides a bias force in a distal direction against the pin.

2. The mechanism of claim 1, wherein the respective first and second pin ends are each received within openings that extends through the collar distal portion.

3. The mechanism of claim 1, wherein the shank annular sidewall defines a distally extending opening within which at least a portion of an instrument is positionable.

4. The mechanism of claim 1, wherein the at least two first slots are positioned diametrically opposed within the collar annular sidewall.

5. The mechanism of claim 1, wherein the at least two second slots are positioned diametrically opposed within the shank annular sidewall.

6. The mechanism of claim 1, wherein the first slot comprises a first slot opening portion that extends in a proximal direction to a first slot capture portion having a first slot capture portion proximal surface spaced from the collar proximal portion, wherein the first slot opening portion extends through the collar sidewall distal end oriented at a first slot opening portion angle with respect to the longitudinal axis A-A.

7. The mechanism of claim 6, wherein the first slot opening portion angle extends between the longitudinal axis A-A and an imaginary plane that bisects a width of the first slot opening portion, and wherein the angle ranges from about 30° to about 60°.

8. The mechanism of claim 6, wherein the first slot capture portion proximal surface has a radius of curvature that ranges from about 0.1 cm to about 2 cm.

9. The mechanism of claim 1, wherein the second slot comprises a second slot cutout portion that extends through the shank annular sidewall at the shank distal end to a second slot traverse portion that extends about perpendicular to the longitudinal axis A-A.

10. The mechanism of claim 1, wherein a first post extends along the longitudinal axis A-A from the collar proximal portion to a first post distal end with a first post distal end surface, the first post distal end surface extending between the interior and exterior collar sidewall surfaces at the first post distal end, and wherein the first post distal end surface is curved.

11. The mechanism of claim 1, wherein an alignment slot is formed between a first post and a second post, the first post adjacent to the second post, the first and second posts extending lengthwise along the longitudinal axis A-A from the collar proximal portion to the collar distal end.

12. A mechanism for connecting an instrument to a driver, the mechanism comprising:
a) a collar comprising a collar annular sidewall defining a collar throughbore that extends along a longitudinal axis A-A from a collar proximal portion having a collar proximal end and a collar annular sidewall proximal end to a collar distal portion having a collar distal and a collar annular sidewall distal end, the collar annular sidewall having a collar annular sidewall thickness spaced between an interior collar sidewall surface and an exterior collar sidewall surface, wherein at least two spaced apart first slots extend through the collar annular sidewall thickness from the collar annular sidewall distal end part way to the collar annular sidewall proximal end and wherein an alignment slot extends longitudinally through the collar annular sidewall distal end partway to the collar proximal end;
b) a shank having an elongated shank proximal portion with a shank proximal end that extends along the longitudinal axis A-A to a shank distal portion with a shank distal end, a shank annular sidewall extending from the shank proximal portion to the shank distal end having a shank annular sidewall thickness oriented perpendicular to the longitudinal axis, wherein;
  a. at least two spaced apart second slots extend through the shank annular sidewall thickness from the shank annular sidewall distal end part way to the shank annular sidewall proximal end;
  b. the shank is disposed within the collar throughbore so that the collar is slidable in an axial direction along the longitudinal axis A-A with respect to the shank, the respective proximal and distal portions of the shank and collar oriented in parallel to the longitudinal axis A-A; and
  c. a protrusion outwardly extends from an exterior surface of the shank, the protrusion extending longitudinally from a protrusion distal end at the shank distal end to a protrusion proximal end spaced from the shank proximal end, wherein the protrusion is received within the alignment slot of the collar so that the protrusion is slidable in an axial direction within the alignment slot;
c) a bias member disposed circumferentially around an exterior surface of the shank proximal portion, wherein the bias member provides a bias force in a distal direction against the collar; and
d) a locking ring having a locking ring annular sidewall that extends along the longitudinal axis A-A from a locking ring proximal end to a locking distal end, wherein the locking ring is connectable to the shank along the shank proximal portion, the bias member being positioned between the shank annular sidewall and the locking ring distal end.

13. The mechanism of claim 12, wherein the shank annular sidewall defines a distally extending opening within which at least a portion of a cutting instrument is positionable.

14. The mechanism of claim 12, wherein the at least two first slots are positioned diametrically opposed within the collar annular sidewall.

15. The mechanism of claim 12, wherein the at least two second slots are positioned diametrically opposed within the shank annular sidewall.

16. The mechanism of claim 12, the first slot comprises a first slot opening portion that extends in a proximal direction to a first slot capture portion having a first slot capture portion proximal surface spaced from the collar proximal portion, wherein the first slot opening portion extends through the collar sidewall distal end oriented at a first slot opening portion angle with respect to the longitudinal axis A-A.

17. The mechanism of claim 16, wherein the first slot opening portion angle extends between the longitudinal axis A-A and an imaginary plane that bisects a width of the first slot opening portion, and wherein the angle ranges from about 30° to about 60°.

18. The mechanism of claim 16, wherein the first slot capture portion proximal surface has a radius of curvature that ranges from about 0.1 cm to about 2 cm.

19. The mechanism of claim 12, wherein the second slot comprises a second slot cutout portion that extends through the shank annular sidewall at the shank distal end to a second slot traverse portion that extends about perpendicular to the longitudinal axis A-A.

20. The mechanism of claim 12, wherein a first post extends along the longitudinal axis A-A from the collar proximal portion to a first post distal end with a first post distal end surface, the first post distal end surface extending between the interior and exterior collar sidewall surfaces at the first post distal end, and wherein the first post distal end surface is curved.

21. The mechanism of claim 12, wherein an alignment slot is formed between a first post and a second post, the first post adjacent to the second post, the first and second posts extending lengthwise along the longitudinal axis A-A from the collar proximal portion to the collar distal end.

22. The mechanism of claim 12, wherein the locking ring comprises a locking ring protrusion that extends from an interior surface of the locking ring annular sidewall towards the longitudinal axis, wherein the locking ring protrusion is received within a locking groove that at least partially extends within an exterior surface of the shank proximal portion.

* * * * *

UNITED STATES PATENT AND TRADEMARK OFFICE
CERTIFICATE OF CORRECTION

PATENT NO. : 10,231,741 B2
APPLICATION NO. : 15/200582
DATED : March 19, 2019
INVENTOR(S) : Jonathan P. Crandall et al.

Page 1 of 1

It is certified that error appears in the above-identified patent and that said Letters Patent is hereby corrected as shown below:

In the Claims

In Column 11, Line 2: in Claim 1, after "protrusion" insert --proximal--; in Column 11, Line 67: in Claim 12, after "distal" insert --end--

In Column 12, Line 18: in Claim 12, delete "wherein;" and insert --wherein:--

Signed and Sealed this
Twelfth Day of November, 2019

Andrei Iancu
*Director of the United States Patent and Trademark Office*